US00PP29376P3

(12) United States Plant Patent
Higaki

(10) Patent No.: US PP29,376 P3
(45) Date of Patent: Jun. 12, 2018

(54) ***HYDRANGEA* PLANT NAMED 'BCHY-10.P14'**

(50) Latin Name: ***Hydrangea macrophylla* (Thunb.)**
Varietal Denomination: BCHY-10.P14

(71) Applicant: Harrison M. Higaki, San Mateo, CA (US)

(72) Inventor: Harrison M. Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days. days.

(21) Appl. No.: 14/999,047

(22) Filed: Mar. 23, 2016

(65) Prior Publication Data

US 2017/0280604 P1 Sep. 28, 2017

(51) Int. Cl.
*A01H 5/02* (2018.01)

(52) U.S. Cl.
USPC ..... Plt./250

(58) Field of Classification Search
USPC ..... Plt./250
See application file for complete search history.

*Primary Examiner* — Keith O Robinson
(74) *Attorney, Agent, or Firm* — James R. Cypher; Charles R. Cypher

(57) ABSTRACT

A new and distinct cultivar of *Hydrangea macrophylla* (Thunb.) named 'BCHY-10.P14' originated as a controlled cross between varieties. The variety 'BCHY-10.P14' has attractive inflorescences with relatively large sepalous florets, attractive, uniform sepal pigmentation and good commercial characteristics.

3 Drawing Sheets

Botanical classification: *Hydrangea macrophylla* (Thunb.) 'BCHY-10.P14'.

Variety denomination: 'BCHY-10.P14'.

BACKGROUND OF THE INVENTION

This invention relates to a new and distinct cultivar of the Saxifragaceae family. The botanical name of the plant is *Hydrangea macrophylla* (Thunb.) 'BCHY-10.P14'.

The new cultivar originated as a seedling from a controlled cross between the commercial variety known to the inventor as 'Blue Danube' which he does not believe is patented and which was the pollen parent and the commercial variety known as 'Venedig' which was the seed parent. The inventor does not think that 'Venedig' is patented. 'Blue Danube' is a relatively compact plant.

The variety 'BCHY-10.P14' has relatively large sepalous florets, uniform sepal pigmentation at maturity and good commercial characteristics. The color of the sepals changes as the plant ages. Below is a table comparing the new variety to similar varieties.

TABLE 1

| | New Variety 'BCHY-10.P14' | U.S. Plant Pat. No. 23,757 'BC6.1' |
|---|---|---|
| Leaf size | 10 cm wide × 14.5 cm long | 12 cm wide × 15 cm long |
| Plant height | 20" in 6" pot. | 15" in 6" pot. |
| Stem strength | Strong | Stems are strong but benefit from being staked |
| Sepal Pigmentation | Upper sides of sepals are R.H.S. 98 A (violet - blue group). Under sides of sepals are R.H.S. 98 C (violet - blue group). | Upper side of sepals is R.H.S. 86 A (violet group); Under side of sepals is R.H.S. 88 D (violet group) |
| Sepalous Floret Size - Diameter | 70 mm | 70 mm |

TABLE 1-continued

| | U.S. Plant Pat. No. 25,507 'BC8.3' | Commerical variety 'Venedig' |
|---|---|---|
| Leaf size | 10 cm × 16 cm | |
| Plant height | 15" in 6" pot | 12" in 6" pot - observed controls grown alongside 'BC6.1'. |
| Stem strength | Stems are relatively strong. | Strong - observed controls grown alongside 'BC6.1'. |
| Sepal Pigmentation | Upper side of sepals is R.H.S. 73A (red - purple group) in center, and margins of sepals are R.H.S. 56 A (red group). | Upper side of sepals is R.H.S. 84 A (violet group). Under side of sepals is R.H.S. 85 A (violet group) observed controls grown alongside 'BC6.1'. |
| Sepalous Floret Size - Diameter | 50 mm to 60 mm | 70 mm - observed controls grown alongside 'BC6.1'. |

The new cultivar 'BCHY-10.P14' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were used from the initially selected plant. Examination of asexually reproduced, successive generations grown in Half Moon Bay, Calif. show that the combination of characteristics as herein disclosed for 'BCHY-10.P14' remains firmly fixed.

DESCRIPTION OF THE DRAWINGS

The accompanying drawings consist of color photographs that show the typical plant form at 50 weeks when grown in a commercial nursery and forced to bloom, including the inflorescence, foliage, and sepals.

DESCRIPTION OF THE NEW PLANT

Figure 1:
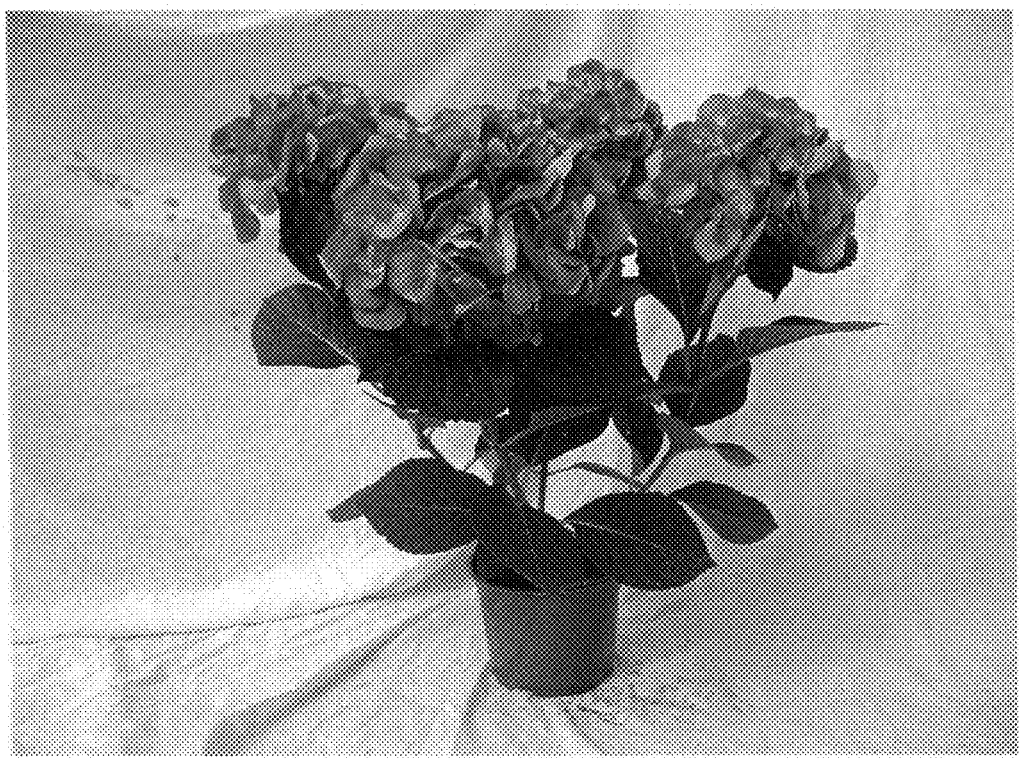
FIG. 1 is a view of the entire plant showing its form, growth habit, dark green foliage, inflorescence, and the color of its sepals.
Figure 2:
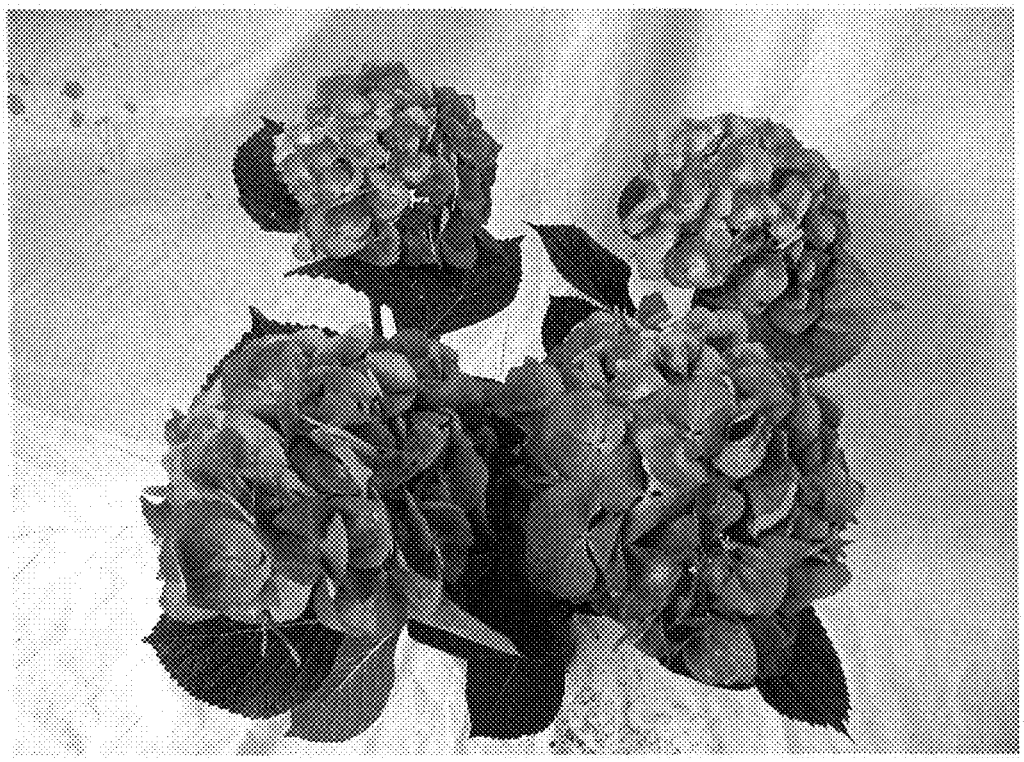
FIG. 2 is a top view of the entire plant showing its form, growth habit, dark green foliage, inflorescence, and the color of its sepals.
Figure 3:
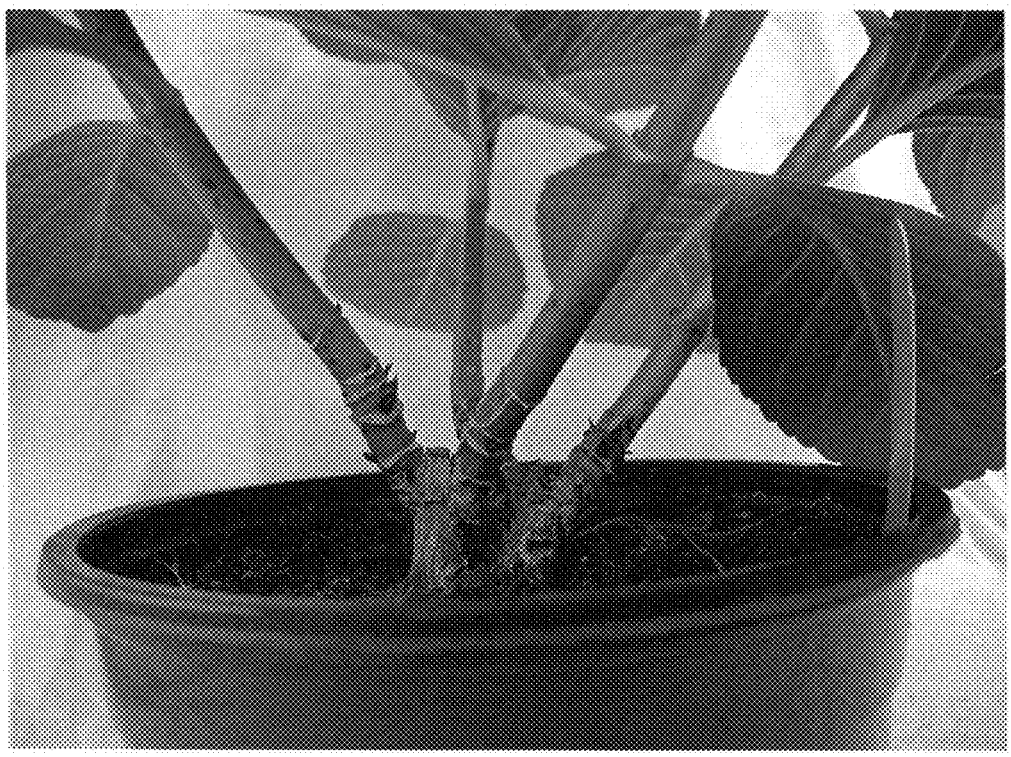
FIG. 3 is a view of the base of the plant.
Figure 4:
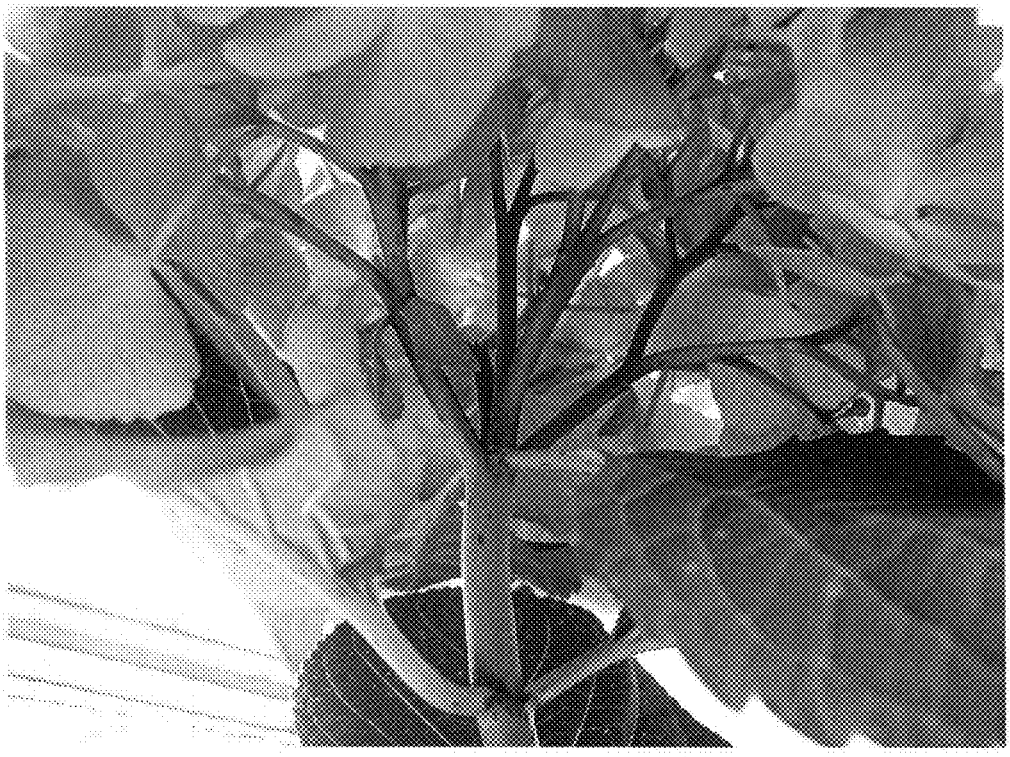
FIG. 4 is a close-up view of the underside of a panicle.
Figure 5:
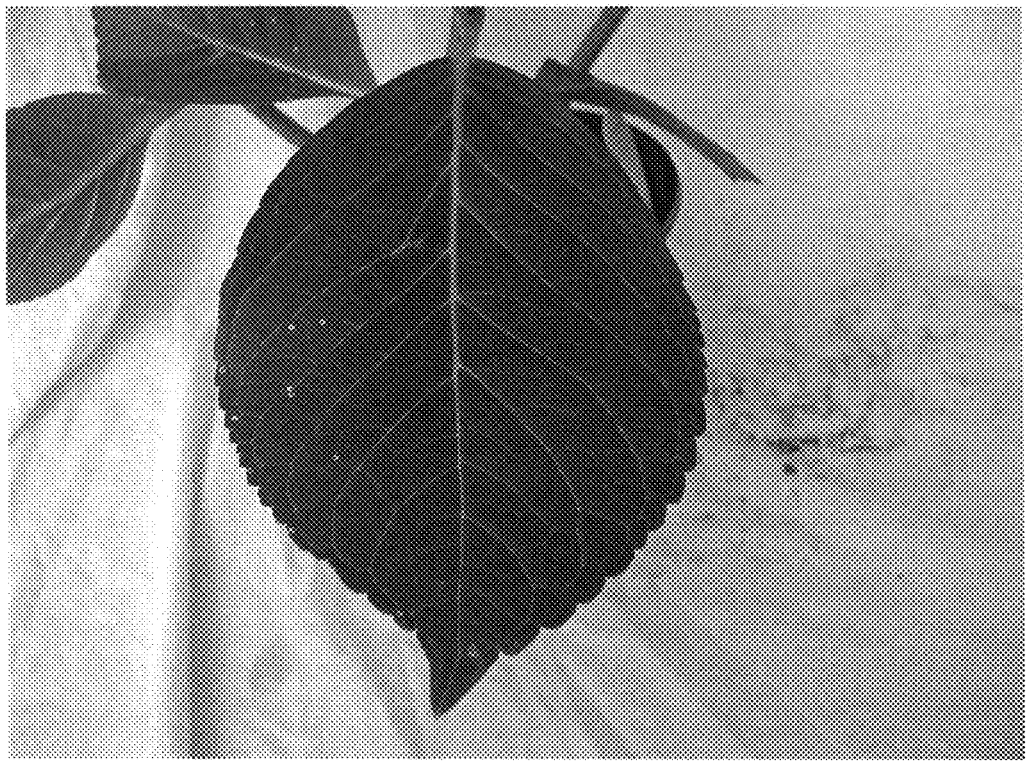
FIG. 5 is a close-up view of the adaxial surface of a mature leaf.
Figure 6:
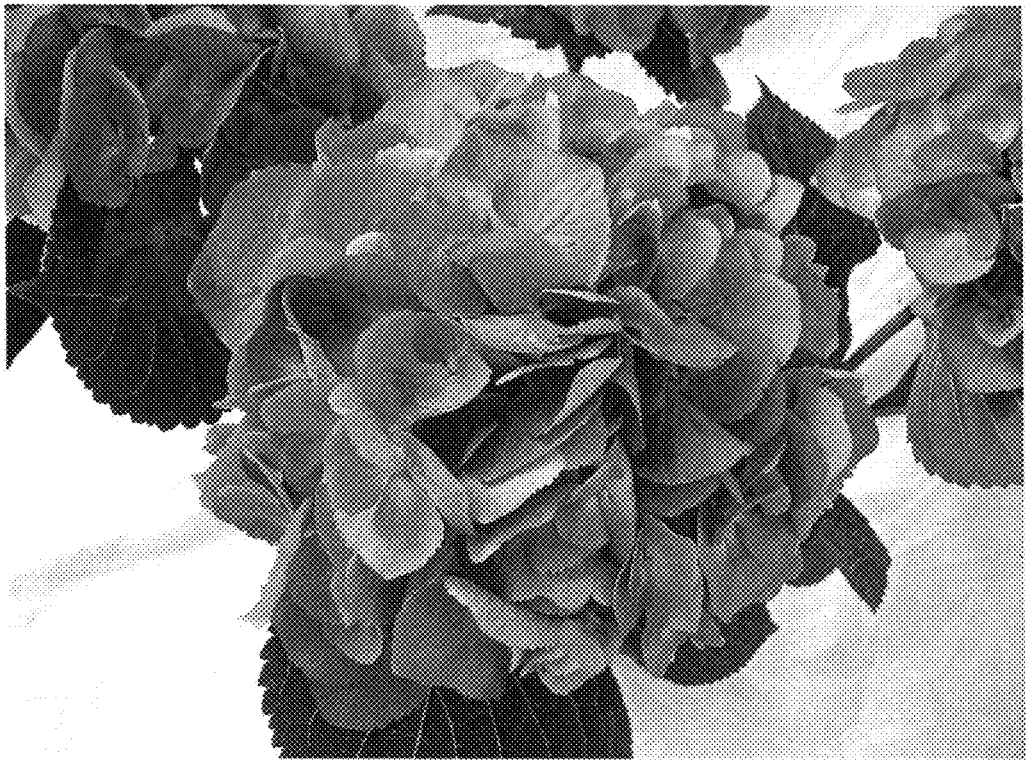
FIG. 6 is a close-up view of the upperside of the inflorescence of the new variety.

The plant described is approximately 50 weeks old. The plant started out as cuttings, used from the stem of a grown plant. The soil for the plant was periodically treated with aluminum to produce blue pigmentation. The plant was pinched early to promote lateral branches.

'BCHY-10.P14' has not been observed under all possible environmental conditions. The phenotype may vary significantly with variations in environment such as temperature, light intensity, treatment with aluminum and day length. Color determinations were made with The Royal Horticultural Society (R.H.S.) Colour Chart, developed in association with the Flower Council of Holland, located in Lieden. The plant:

*Origin*.—Controlled cross. The new cultivar originated as a seedling from a controlled cross between the commercial variety known as 'Venedig' which was the seed parent and the commercial variety 'Blue Danube' which was the pollen parent.

*Form*.—Upright, compact shrub. The mature plant including a mature inflorescence that is ready for sale is approximately 20" high and has a diameter of 22" when grown in a 6" pot with appropriate soil amendments.

*Growth*.—Upright, vigorous growth habit. Inflorescence is large. The plant branches easily with shoots forming at the base of the plant. Lateral branches are similar in appearance and form to the main stems.

*Stems*.—Stems are 15" long. Fasciation is absent. Lenticels are present. Lenticels are R.H.S. 86 A (violet group) and are 1 to 4 mm long. The surface of young stems is glabrous. Stems become woody as they age. The color of typical young stems and young lateral branches is R.H.S. 144 A (yellow-green group). The older portions of the stems are R.H.S. 199 A (grey-brown group). Younger portions of the stems are 7 mm in diameter. Older portions of the stems are 7 mm in diameter.

*Foliage*.—Abundant. Leaves are opposite on stem and lateral branches. Shape of leaf. — Elliptic with acute base and acute apex. Leaf blade margins are serrate and not lobed. Texture. — Glabrous; veins dominate on the underside of the leaf and are sunken on the upper leaf surface. Color. — Mature leaves have an upper side that is R.H.S. 136 A (green group), and an under side that is R.H.S. 137 C (green group). Leaves are moderately glossy. Variegation is absent. Leaves are pinnately veined. The midvein and veins branching off the midvein are large and prominent on the underside of the leaves. Veins are R.H.S. 145 C (yellow-green group). Leaves are as wide as 10.0 cm and 14.5 cm long. Petioles are smooth and approximately 3.0 cm long and 4 mm wide. Petioles are R.H.S. 145 C (yellow-green group).

Buds:

*Form*.—Globose with 4 to 5 connate, elliptic, smooth petals. Most buds, whether they will mature into sepalous or non-sepalous florets, have 4 petals. Buds in the center of the inflorescence are non-sepalous. The minority of buds will develop into sepalous florets. They are approximately 2 mm by 2 mm when very young. Buds can be 5 mm in diameter and still unopened. Color of mature buds is R.H.S. 98 B (violet-blue group).

*Aspect*.—Smooth.

*Arrangement*.—Borne on branched panicles.

Inflorescence:

*Form*.—Paniculate. Terminal. Globose. As many as 100 individual florets (both sepalous and non-sepalous) per inflorescence. Both sepalous florets and non-sepalous florets borne on the same panicle. Flowers do not produce a fragrance. The peduncle for the inflorescence is strong and upright. Very few non-sepalous florets developing early on cymes that are later hidden by sepalous florets that form at the outside of the panicle. Florets, both sepalous and non-sepalous, have anthers and style. Inflorescences are long-lasting.

*Size of inflorescence*.—Compact and globose. Individual inflorescence size is dependent on the number of florets. A typical inflorescence can grow as large as 9" in diameter, and 5" high.

*Shape*.—Clusters of numerous small florets; sepalous florets overlap one another. Sepals are persistent.

*Appearance*.—Showy.

Florets:

*General*.—The non-sepalous florets at the center of the inflorescence open first. Sepalous and non-sepalous florets are perfect and complete. Corolla: Generally, for both sepalous and non-sepalous florets there are 4 petals. Petals are typically 4 mm long and 3 mm wide. Petals are R.H.S. 98 B (violet-blue group). Lenticels are present on pedicels of both sepalous and non-sepalous florets, lenticels are no more than 1 mm. Lenticels are R.H.S. 59 B (red-purple group). Pedicel length for non-sepalous florets averages 4 mm. Pedicel length of sepalous florets is approximately 40 mm in length for plants of this age. Pedicels of both sepalous and non-sepalous florets continue to elongate as the inflorescence ages. Pedicels range from 98 B (violet-purple group) to R.H.S. 145 D (yellow-green group) near floret when immature.

*Stamens*.—8 to 10 stamens. Anther is regular and basally attached.

*Stigma*.—Two to three style each, although most florets have two style. Each style has one stigma.

*Ovary*.—Ovary is partially inferior.

*Sepalous florets*.—General. — Veins dominate on the underside of the sepals. Number of sepals. — 4 to 5 sepals per floret, usually 4. Aspect of sepals. — Smooth and glaucescent. Shape of sepals. — Reniform with acuminate apex. Edges are entire, but with much crenation. Size of sepals. — As the florets mature, the sepals enlarge and overlap each other more and more, until, often, there is no space between the sepals when the petals of the florets open. Sepals at maturity are typically 32 mm long and 40 mm wide. Sepalous florets are typically 70 mm in diameter. The upper sides of the sepals are R.H.S. 98 A (violet-blue group) and the undersides are R.H.S. 98 C (violet-blue group). Pigmentation develops at the tips of the sepals and travels inward towards base of the sepals.

*Fruit*.—None.

*Disease and pest resistance*.—Unknown. Plants prefer milder temperatures. Plants bloom in the spring but can be forced to bloom by placing in a cold environment.

I claim:

1. A new and distinct *Hydrangea macrophylla* plant named 'BCHY-10. P14' substantially as herein illustrated and described.

* * * * *